United States Patent [19]

Rubel et al.

[11] 4,216,780
[45] Aug. 12, 1980

[54] APPARATUS FOR THE ACQUISITION AND PRE-PROCESSING OF ELECTROCARDIOGRAPHIC DATA

[75] Inventors: Paul Rubel; Pierre Arnaud, both of Lyon, France

[73] Assignee: Institut National de la Sante et de la Recherche Medicale, Paris, France

[21] Appl. No.: 911,018

[22] Filed: May 30, 1978

[30] Foreign Application Priority Data

May 31, 1977 [FR] France ............................. 77 16462

[51] Int. Cl.² ............................................. A61B 5/04
[52] U.S. Cl. ................................................. 128/699
[58] Field of Search ............... 128/2.06 V, 2.06 B, 128/2.06 G, 2.06 R, 2.1 A, 696, 699, 709, 710, 901, 902, 904

[56] References Cited

U.S. PATENT DOCUMENTS

| 2,684,278 | 7/1954 | Marchand | 128/2.06 B |
| 3,699,948 | 10/1972 | Ota et al. | 128/2.06 G |
| 3,830,228 | 8/1974 | Foner | 128/2.06 R |
| 3,868,948 | 3/1974 | Graetz | 128/2.06 B |
| 4,124,894 | 11/1978 | Vick et al. | 128/2.06 A |

Primary Examiner—William E. Kamm
Attorney, Agent, or Firm—William A. Drucker

[57] ABSTRACT

Apparatus for the acquisition and pre-processing of electrocardiographic data.

It comprises elements for multiplexing (1) and pre-amplifying (2) signals picked up by the 7 electrodes, in a Frank network (3), of three fixed gain amplifiers (4, 5, 6), a 12-bit analog-to-digital converter (8), a device (9) for digit compression of the signals, a micro-processor (11) and display elements (20), all these elements being assembled in a portable unit.

Application to the processing of vectocardiographic data.

13 Claims, 9 Drawing Figures

| N | $S_{12}$ | $S_{11}$ | $S_{10}$ | $S_9$ | $S_8$ | $S_7$ | $S_6$ | $S_5$ | $S_4$ | $S_3$ | $S_2$ | $S_1$ |
|---|---|---|---|---|---|---|---|---|---|---|---|---|
| 7 | 1 | $A_6$ | $A_5$ | $A_4$ | $A_3$ | $A_2$ | $A_1$ | X | X | X | X | X |
| 6 | 0 | 1 | $A_6$ | $A_5$ | $A_4$ | $A_3$ | $A_2$ | $A_1$ | X | X | X | X |
| 5 | 0 | 0 | 1 | $A_6$ | $A_5$ | $A_4$ | $A_3$ | $A_2$ | $A_1$ | X | X | X |
| 4 | 0 | 0 | 0 | 1 | $A_6$ | $A_5$ | $A_4$ | $A_3$ | $A_2$ | $A_1$ | X | X |
| 3 | 0 | 0 | 0 | 0 | 1 | $A_6$ | $A_5$ | $A_4$ | $A_3$ | $A_2$ | $A_1$ | X |
| 2 | 0 | 0 | 0 | 0 | 0 | 1 | $A_6$ | $A_5$ | $A_4$ | $A_3$ | $A_2$ | $A_1$ |
| 1 | 0 | 0 | 0 | 0 | 0 | 0 | 1 | $A_6$ | $A_5$ | $A_4$ | $A_3$ | $A_2$ |
| 0 | 0 | 0 | 0 | 0 | 0 | 0 | 0 | $A_6$ | $A_5$ | $A_4$ | $A_3$ | $A_2$ |

| $A_{10}$ | $A_9$ | $A_8$ | $A_7$ | $A_6$ | $A_5$ | $A_4$ | $A_3$ | $A_2$ | $A_1$ |
|---|---|---|---|---|---|---|---|---|---|
| 1 | 1 | 1 | 1 | $A_6$ | $A_5$ | $A_4$ | $A_3$ | $A_2$ | $A_1$ |
| 1 | 1 | 1 | 0 | $A_6$ | $A_5$ | $A_4$ | $A_3$ | $A_2$ | $A_1$ |
| 1 | 1 | 0 | 1 | $A_6$ | $A_5$ | $A_4$ | $A_3$ | $A_2$ | $A_1$ |
| 1 | 1 | 0 | 0 | $A_6$ | $A_5$ | $A_4$ | $A_3$ | $A_2$ | $A_1$ |
| 1 | 0 | 1 | 1 | $A_6$ | $A_5$ | $A_4$ | $A_3$ | $A_2$ | $A_1$ |
| 0 | 1 | 1 | 0 | $A_6$ | $A_5$ | $A_4$ | $A_3$ | $A_2$ | $A_1$ |
| 0 | 1 | 0 | 1 | $A_6$ | $A_5$ | $A_4$ | $A_3$ | $A_2$ | 0 |
| 0 | 0 | 1 | 0 | $A_6$ | $A_5$ | $A_4$ | $A_3$ | 0 | 0 |
| 0 | 0 | 0 | 0 | $A_6$ | $A_5$ | $A_4$ | $A_3$ | 0 | 0 |

Fig. 8

APPARATUS FOR THE ACQUISITION AND PRE-PROCESSING OF ELECTROCARDIOGRAPHIC DATA

The invention concerns systems for the acquisition and processing of electrocardiographic data and in particular electrocardiography systems with three orthogonal branch circuits such as those which apply Frank's network.

Such systems are designed to supply, in real or deferred time, the medical interpretation of the signals. They therefore comprise a computer linked to an acquisition head comprising elements for multiplexing, pre-amplifying and converting the signals picked up by the electrodes, elements to amplify the scalar components resulting from the conversion and elements for displaying these components with a view to carrying out the essential verifications of the proper working of the acquisition head.

These verifications are, in general, carried out visually by the operator on the acquisition head and controlled manually, while some operations, termed "pre-processing" of data, are carried out by the computer.

The result of this previous design of the system is that the acquisition process is relatively long and sometimes requires the patient to be present several times.

The aim of the invention is to make the verifications entirely automatic, without thereby eliminating the possibility of constant visual verifications, and to eliminate recourse to a distant computer to carry out pre-processing.

It makes it possible to carry out a complete acquisition and pre-processing procedure in about ten minutes, at the same time improving the validity of the results.

According to the invention, the acquisition head is associated with analog-to-digital conversion means and a micro-processor in the same portable unit, and the micro-processor is programmed to apply calibration pulses to the input of the pre-amplification, conversion and amplification chain when the apparatus is switched on and to analyse the response of the chain to said pulses; to control an operation to return to zero the base line of the scalar components on the one hand, at fixed intervals corresponding to a length of acquisition sequences which follow on automatically, and on the other hand at the beginning and end of calibration; and to carry out the main pre-processing operations.

According to a preferred form of embodiment, said display elements are arranged to allow real time observation of the curves during acquisition of data and, during the verification of the signals, the movement of the curves in one direction or other at a controllable speed or their stoppage and the introduction of an adjustable reduction factor or magnifying-glass effect.

According to a peculiarity of the invention, the amplifiers are fixed gain amplifiers and said analog-to-digital conversion elements include a device for digit compression of the data and the micro-processor is programmed to carry out the unpacking and standardisation of data before the typical complex selection phase.

Other peculiarities, as well as the advantages of the invention, will emerge clearly from the following description.

Figure 1:
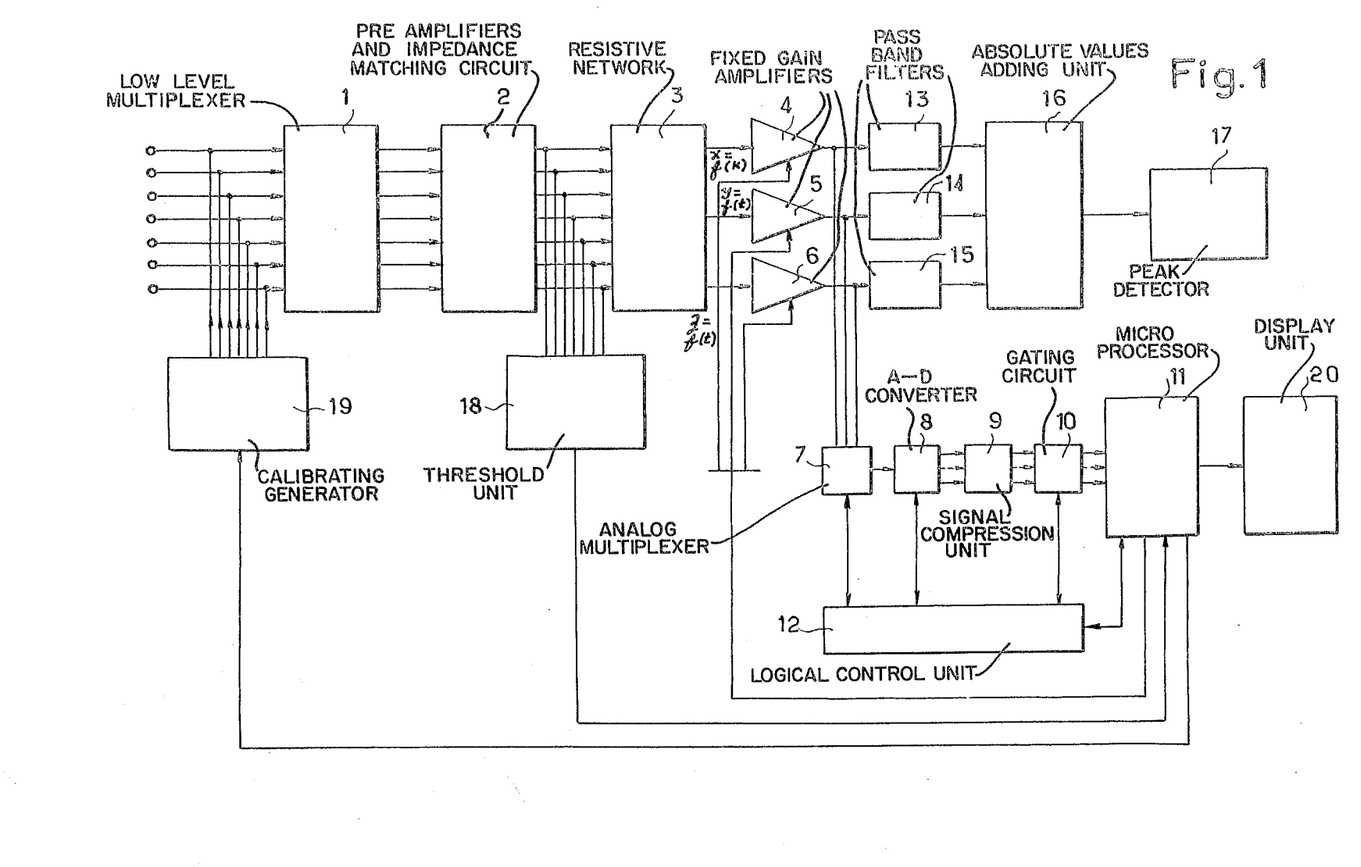
FIG. 1 is a general diagram of an apparatus for acquisition and pre-processing according to the invention.

In the vectocardiographic (VCG) data acquisition head shown in FIG. 1, the 7 electrodes, arranged according to Frank's orthogonal system, are connected, via a low level multiplexer 1 and a device 2 comprising 7 buffer pre-amplifier elements and impedance adapters, to a Frank resistive network 3 which supplies, in a way known in itself, the three VCG signals $X=f(t)$, $Y=f(t)$ and $Z=f(t)$. These are applied to three fixed gain amplifiers 4, 5 and 6 respectively. The outputs of these amplifiers are connected via an analog multiplexer 7 to a 12-bit analog-to-digital converter 8, itself connected to a system of gates 10 via a signals compression device 9. The outputs of the system of gates 10 are connected to a micro-processor 11. A logical control unit 12 assumes the functions which will be explained later.

Moreover, the outputs of amplifiers 4, 5 and 6 are connected, via pass-band filters 13, 14 and 15, to a device 16 capable of adding up, as will be explained later, the absolute values of the three channels. This device is itself followed by a peak detector 17. A threshhold device 18 is connected in parallel to the outputs of the pre-amplifiers 2. This device detects the saturation of the pre-amplifiers which occurs notably in case of faulty contact between an electrode and the skin. When this saturation occurs, the apparatus recommences recording.

Finally, the elements displaying the signals connected to the micro-processor 11 have been symbolised by a block 20. The system for the acquisition and pre-processing of data so formed combines, in the same portable unit, the acquisition elements and the micro-processor, the latter automatically carrying out a certain number of verifications ensuring the safe interpretation of the vectocardiogram and, in applications where this is necessary, a certain number of automatic operations termed "pre-processing".

The whole of these operations and these verifications will not be described, only those which are carried out in an original manner.

A first verification operation consists of the calibration of the acquisition chain, which is carried out automatically after a voltage has been applied. It is preceded and followed, as will be explained later, by an operation to return to zero the base line ("clamping") lasting 50 ms.

A 1 mV calibrating generator 19 is substituted for the 7 electrodes in order to apply 7 rectangular signals to the input of multiplexer 1, such as to obtain three rectangular signals of 1 mV each at the output of the Frank network 3. Generator 19 comprises an analog calculation network derived from the Frank network and whose construction is within the scope of a person skilled in the art.

The micro-processor is programmed to start up the operation of generator 19 at a clearly defined time and for a clearly defined length of time and to verify whether the response of the amplifiers is correct. For this purpose, it calculates the gain and the pass-band of the amplifiers and determines whether this response is acceptable or not. In the latter case, the calibration operation is repeated after adjustment.

The mean value of the three output signals from the amplifiers is determined by the micro-processor, stored and edited.

A second phase consists of a data acquisition procedure, such as the one which will be described later, but with no enabling of the recording at the micro-processor. There is simply constant display of the last four seconds of acquisition and the three "scalars" (signals coming from the amplifiers) are examined by the operator, who can thus see if the electrodes are not correctly applied, if there are myograms, etc.

A third phase consists of the recording proper. This begins, after operating a "triggering" button which enables recording, with a 50-msec clamping. Data acquisition stops automatically after 8 seconds. The display device 20 is arranged so that the operator constantly sees the last four seconds of the recording. The way in which this result is obtained will be explained later.

If the operator notes the presence of artefacts, a drift from the base line, or any other defect, he re-starts the recording, possibly after adjustments.

In addition to the visual verification, provision is advantageously made for automatic detection, in the micro-processor, of possible disturbances of the signal.

A first disturbance is the drift from the base line. On each channel, the micro-processor carries out a low-pass filtration at 1 or 2 Hz, followed by a derivative calculation. Detection of a derivative above a certain threshold sets off an alarm and another clamping, followed by a further data acquisition.

A second disturbance consists of artefacts. The micro-processor, after having made a digital detection of the Q R S peaks, determines, between two consecutive peaks, an interval of 200 ms whose middle coincides with the middle of the interval (RR). It then effects a highpass filtration at 30 Hz which also eliminates the T-wave. It calculates the energy of the signal in each of the intervals. Energy exceeding a specific threshold sets off an alarm, clamping and further acquisition.

In short, acquisition continues automatically until 8 seconds of correct signal have been obtained.

During the whole of the three phases which have just been described, the operator can verify, by means of the display, whether the signal is being clipped. Moreover, the micro-processor detects the exceeding of the capacity of the analog-to-digital converter and then supplies a signal which lights up a clipping signal lamp and a clamping command signal.

Figures 2, 9:
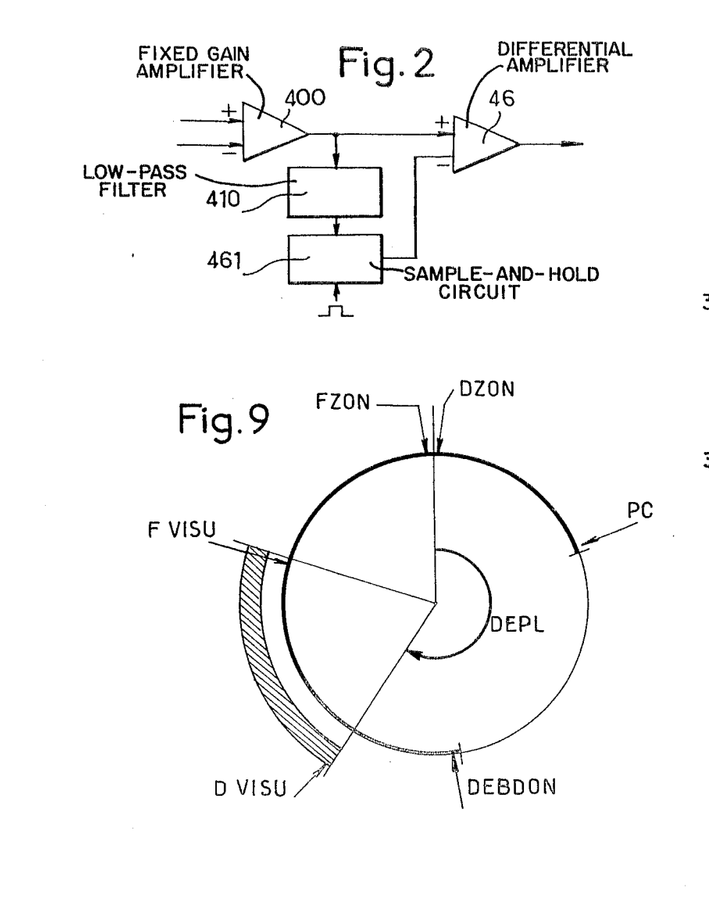
FIG. 2 illustrates the clamping device with which the amplifiers are fitted.
FIG. 8 is a general diagram of a display device comprised in the apparatus of the invention and FIG. 9 illustrates the working of this display device.

Clamping is illustrated in FIG. 2. Each of the amplifier means 4 - 5 - 6 (FIG. 1) in fact includes a first amplifier 400 (FIG. 2), a filter 410, a sample-and-hold circuit 461 and a differential amplifier 46. Every 8 seconds (or more accurately, every 8.142 seconds, the time a recording lasts) and, in addition, every time clipping is detected, the micro-processor sends a clamping signal (50 ms gating pulse) to the sample-and-hold circuit. The latter then stores the averaged value of the signal and subsequently applies it to the negative terminal of the differential amplifier 46. The latter, therefore, only transmits the voltage variation due to the signal, to the exclusion of the very low frequency component of the much higher voltage corresponding to the base line. This result is obtained with no capacitive link between the two amplifiers 400 and 46, which has the advantage of transmitting the continuous component of the signal, therefore not disturbing the T-wave or the ST-segment.

Filter 410 is a low-pass filter with a cut-off frequency equal to approximately 1 Hz, designed to follow the evolution of the base line, it makes it possible to store, in the sample-and-hold circuit 461, a value corresponding to that of the base line even if clamping occurs at the peak of a Q R S. This is essential for the base line to remain close to zero at the output of amplifier 46. The software provides for enabling the start of the recording stored in such a way as to make this recording start at the start of a P Q R S T sequence.

When the operator, at the end of the third phase, has 8 seconds of recording, he verifies it accurately and selects a typical Q R S complex which he places in the middle of the screen and whose recording will finally be enabled. The recording device is, in fact, arranged so that the complex to be selected can be placed in the middle of the screen and enlarged over the width (i.e. display will correspond to 8, 4, 2, 1 or 0.5 sec.).

The manner in which this result is obtained will be explained later.

A fifth phase consists of the pre-processing carried out automatically by the micro-processor.

It includes a certain number of operations carried out in a way known in itself, such as: determination of the base line by low-pass filtration; calculation of the curve of the module or sum of absolute values; calculation of the RR interval; determination of the complexes similar to the typical complex; obtaining an averaged complex; automatic determination of the start and end of the complexes on the averaged complex. These operations are carried out automatically by the micro-processor.

However, the known operation of accurately determining the peaks of the Q R S complexes is carried out in an original manner, by means of device 16–17 (FIG. 1).

Element 16 is made up, in a way known in itself, of 3 high-pass filters which eliminate parasite frequencies and the very low frequency, followed by three amplifiers fitted to transmit the respective absolute values of three signals, themselves followed by an adding amplifier.

Figure 3:
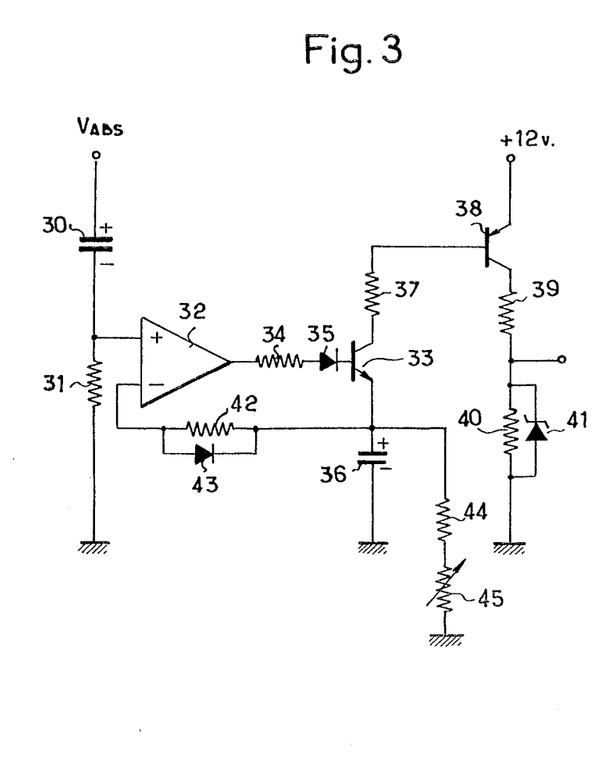
FIG. 3 is a diagram of a crest sensor which forms part of a device for the accurate determination of the peaks of the QRS complexes.

The crest sensor 17 is shown in FIG. 3. The VABS signal coming from element 16 is applied, through a high-pass filter consisting of a capacitor 30 and a resistor 31, to the positive input of a follower amplifier 32. The output of this amplifier is connected to the base of an n-p-n transistor 33 via a resistor 34 and a diode 35. The transmitter of transistor 33 is grounded via a capacitor 36, while its collector is connected, via a resistor 37, to the base of a p-n-p transistor 38, whose transmitter is connected to a +12 v supply. The collector of transistor 38 is grounded via two resistors in series 39 and 40. A Zener diode 41 is connected in parallel to resistor 40. The negative terminal of amplifier 32 is connected to the positive electrode of capacitor 36 by a resistor 42 in parallel with a diode 43. The positive electrode of capacitor 36 is itself grounded by two resistors in series, 44 and 45, one of which is adjustable.

Figure 4:
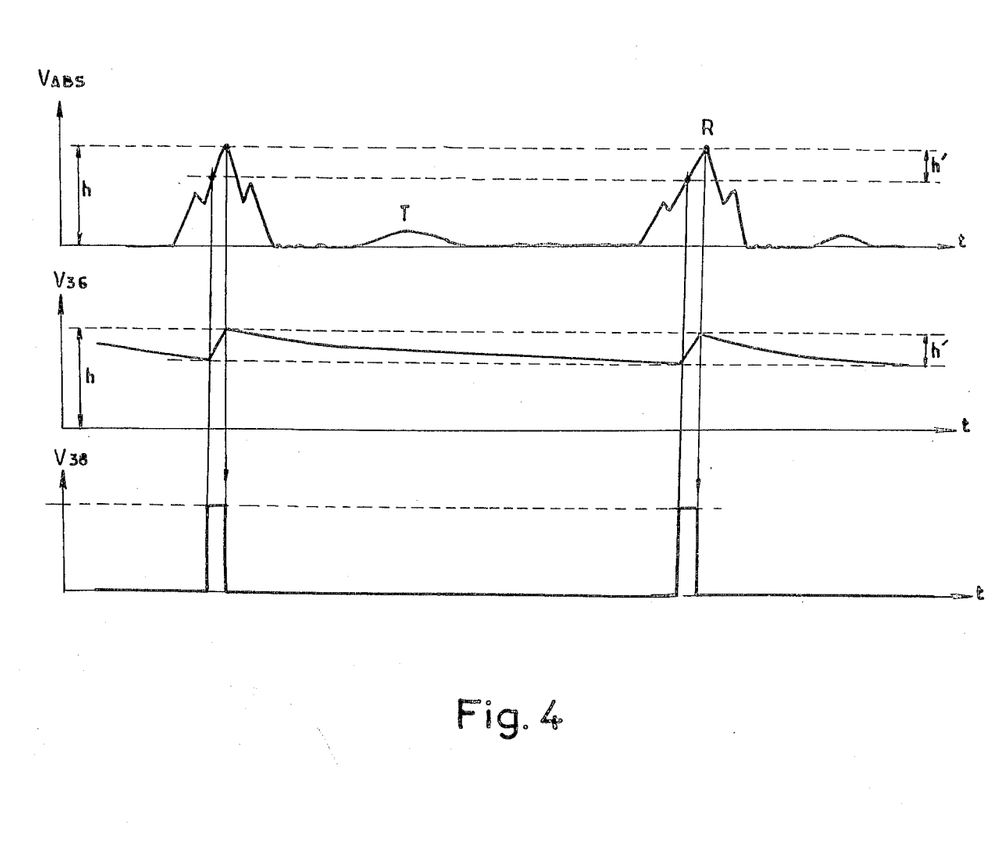
FIG. 4 illustrates the working of the above device.

FIG. 4 illustrates the working of the circuit. The input voltage is represented by the waveform $V_{ABS}$; R is the peak of the Q R S complex.

Capacitor 36 stores the crest value h corresponding to a peak, discharges slowly, through resistors 44, 45 which are adjusted so that, when passing to the next peak, the charge of capacitor 36 has decreased by $h'$, drift $h'$ being e.g. equal to 35% of $h$.

Transistors 33 and 38 are only released when the base voltage of 33 becomes higher than its transmitter voltage, that is to say when, drift $h'$ being reached, $V_{ABS}$ becomes higher than the voltage at the terminals of capacitor 36. As soon as peak S is exceeded, the discharge of capacitor 36 being slower than the reduction of voltage $V_{ABS}$, transistor 33 locks. Waveform $V_{38}$ represents the voltage at the common point of resistors 39 and 40. The amplitude of the gating pulse obtained is fixed at 5.6 v by Zener diode 41.

It is the rear edge of this gating pulse which indicates peak R.

It will be seen that even if the T-wave is large, there is no risk of committing the error of detecting the peak. Moreover, the drift of the base line does not interfere with detection since, between two peaks, it will always be less than $h'$.

The automatic pre-processing phase is followed by a visual verification of the pre-processing phase which makes it possible to correct, if necessary, the complex start and end position determined automatically.

The data edition phase is carried out in a known manner.

Figure 5:
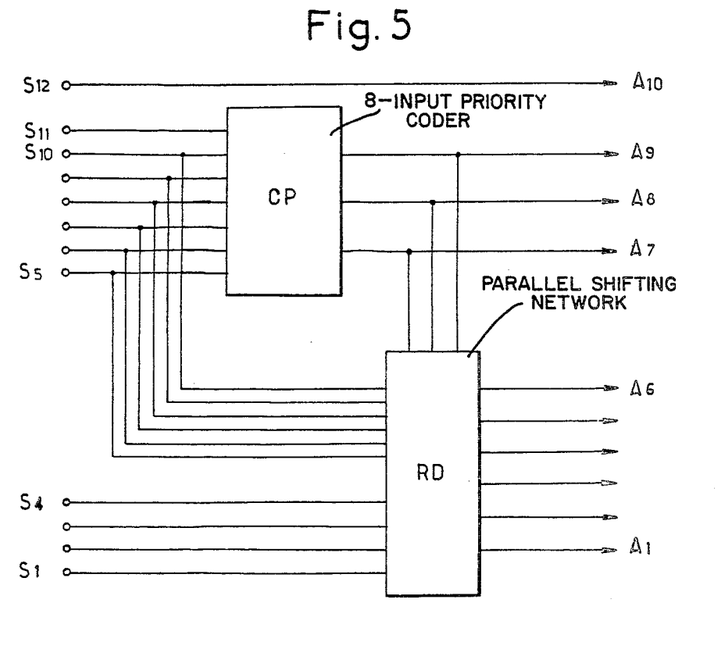
FIG. 5 shows a digit compression device and FIGS. 6 and 7 illustrate the working thereof.

The digit compression device (9 FIG. 1), illustrated in FIG. 5, will now be described. The input signal comprises 11 significant bits $S_1$ to $S_{11}$ and a sign bit $S_{12}$.

Figure 6:
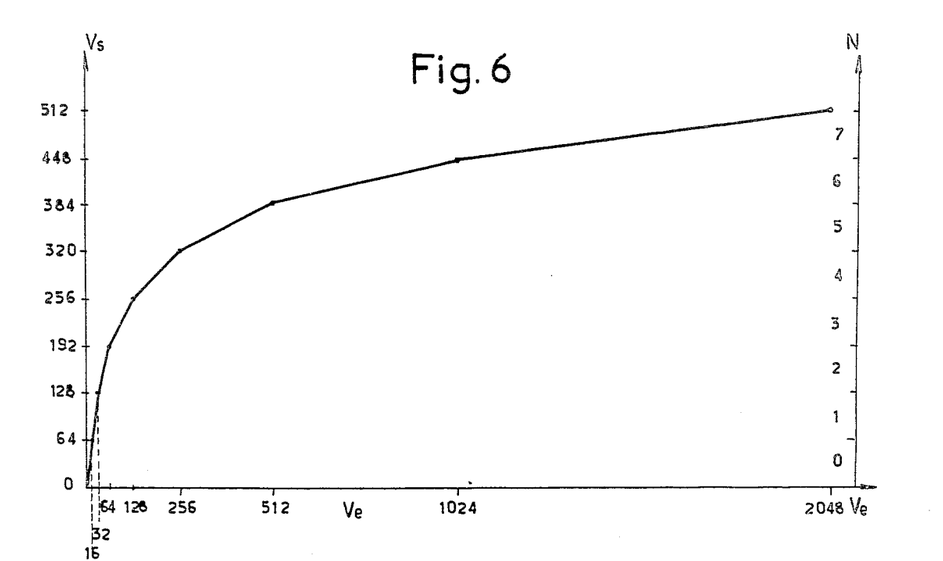

FIG. 6 shows the (10-bit) compressed signal $V_s$ in terms of $V_e$, the ratio of the voltage at the input of the compressor and the maximum value of this voltage.

The law of compression is the A-type used in teletransmission, viz:

$$V_s = \frac{1 + \log A V_e}{1 + \log A} \text{ for } 1/A \leq V_e \leq 1 \text{ and}$$

$$V_s = \frac{A V_e}{1 + \log A} \text{ for } 0 \leq V_e \leq 1/A, \text{ with } A = 87.6$$

The curve $V_s = f(V_e)$ is integrated, by approximation, into 13 straight line segments, defined as follows:

| Segment number N | Input voltage | Digital value |
| --- | --- | --- |
| 0 | 0.00 to 0.80 mV | 0 to 16 |
| 1 | 0.080 to 0.156 mV | 16 to 32 |
| 2 | 0.156 to 0.313 mV | 32 to 64 |
| 3 | 0.313 to 0.625 mV | 64 to 128 |
| 4 | 0.625 to 1.25 mV | 128 to 256 |
| 5 | 1.25 to 2.5 mV | 256 to 512 |
| 6 | 2.5 to 5.0 mV | 512 to 1024 |
| 7 | 5.0 to 10.0 mV | 1024 to 2043 |

Segments 0 and 1 are merged. Segments not indicated would correspond to negative values.

It can be seen that each segment corresponds to 64 compressed signal levels.

Figure 7:
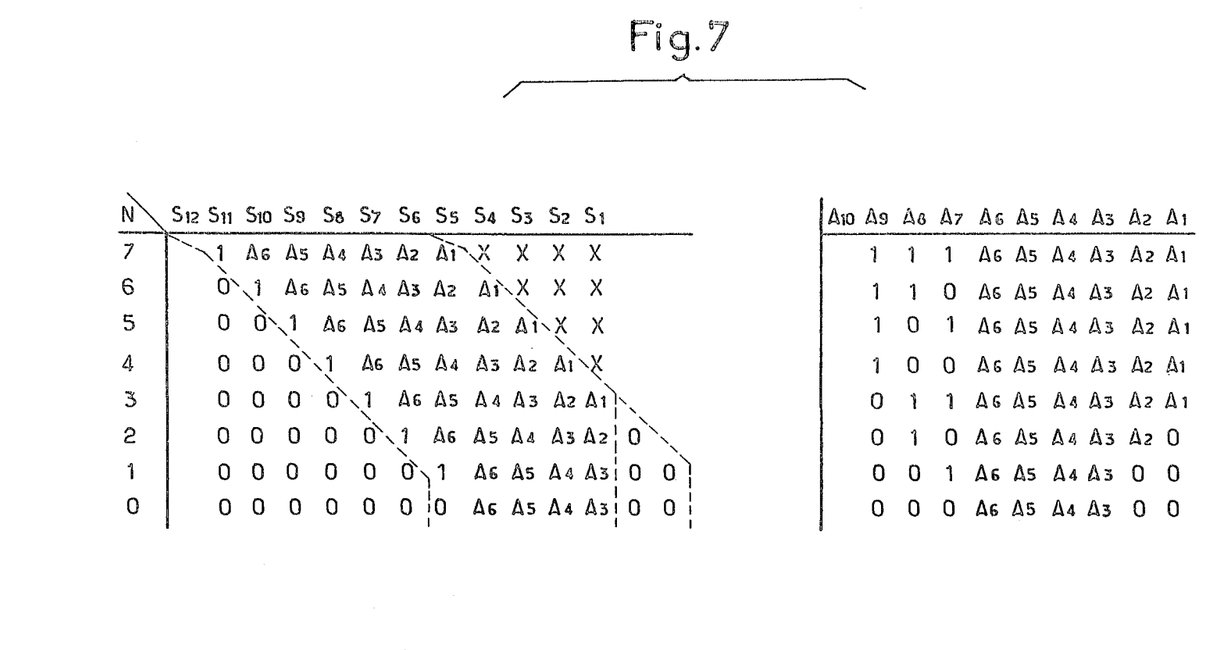

FIG. 7 is a correspondence table between linear code $C_L$ at the compressor input and the compressed output code $C_c$.

Sign bits $S_{12}$ is purely and simply transmitted by the compressor and gives bit $A_{10}$ of the compressed code. The first 1-bit, among $S_{11}$ to $S_5$, defines the number of the segment to which the input voltage belongs (with the exception of segment 0) and corresponds to bits $A_7$, $A_8$, $A_9$ of the compressed code which define this segment in linear code.

Take, for example, an input voltage with a digital value of 379. It corresponds to segment 5 and 123 units beyond the start of the segment. It can therefore be coded as follows:

00 101 1110 11, bits $S_{11}$, $S_{10}$, $S_9$ here defining segment No. 5 and bits $S_8$ to $S_1$ defining the difference 123.

The compressed voltage will belong to segment No. 5 and will be defined by $64 \times 123/256$ units beyond the start of that segment, i.e., approximately, 30 units, which will be written:

10 1011 110.

It can be seen that bits $A_9$ to $A_7$ in the compressed number define the 5th segment whereas bits $A_6$ to $A_1$, which define the position of the compressed voltage in the segment, correspond to the six most significant bits, $S_8$ to $S_3$, in the number which defines the position of the input voltage in the segment.

This law is general, as is shown by the table in FIG. 7, except for the fact that, for segments 0, 1 and 2, the bits which are non-existent in the linear code have to be replaced by 0s in the compressed code.

Returning to FIG. 5, it can be seen that input bits $S_5$ to $S_{11}$ are applied to an 8-input priority coder (PC). The input with the lowest priority is connected to a level 1 voltage supply and the order of prorities goes from $S_5$ to $S_{11}$. It is known that such a device supplies, when one of its inputs is at 1, an output signal which defines the rank of this input, providing that all higher ranking inputs are at 0, and irrespective of the level applied at the lower ranking inputs. It is easy to see that it will give outputs $A_9$, $A_8$, $A_7$ in the table in FIG. 7. By way of example, it may be in accordance with Texas Instruments' Model 74148.

Inputs $S_1$ to $S_{10}$ are applied to a parallel shifting network with 10 SN inputs, of which 6 outputs supply bits $A_1$ to $A_6$ of the compressed code. This network holds, in order to transmit them to outputs $A_6$ to $A_1$, the 6 bits which follows the first 1. In other words, for an input voltage such that a 1 appears on $S_{11}$, it connects inputs $S_{10}$ to $S_5$ to the respective outputs $A_6$ to $A_1$; for an input voltage such that a 1 appears on $S_{10}$, it connects inputs $S_9$ to $S_4$ to the respective outputs $A_6$ to $A_1$, etc.

It inserts zeros into the outputs instead of the missing bits.

Such a device can be embodied by two Signetics "Model 8243 8-bit position scalers".

It should be stressed that the use of a digit compressor makes it possible to use fixed gain amplifiers, despite the considerable dynamics of the signal (40 db) while retaining sufficient accuracy (of the order of 0.5%). The use of an amplifier with manually adjustable gain is not desirable when the micro-processor makes it possible to eliminate all manual intervention. The use of an amplifier with programmable gain would have the drawback that the presence of artefacts might lead to the need to modify the gain adjustment programme during one and the same experiment, which is not desirable.

While the use of a 12-bit analog-to-digital converter makes it possible in practice to avoid gain adjustment, it is very costly to store 12 bits in a micro-processor whose memory is organised in 8-bit bytes. Moreover, a non-compressed signal would be displayed, on a control oscilloscope, in too-small dimensions.

Of course, the compressed data will have to undergo a reverse unpacking operation, which consists of reconstituting a 12-bit signal from the 10-bit signal, and a standardisation operation by means of which the maximum signal will be expressed by 8 bits. These operations, carried out automatically by the micro-processor between phases 3 and 4 described above, facilitate teletransmission of data and allow the operator to carry out verifications (phase 4 above) on an uncompressed signal, but nevertheless occupying the whole of the available area of the screen.

Figure 8:
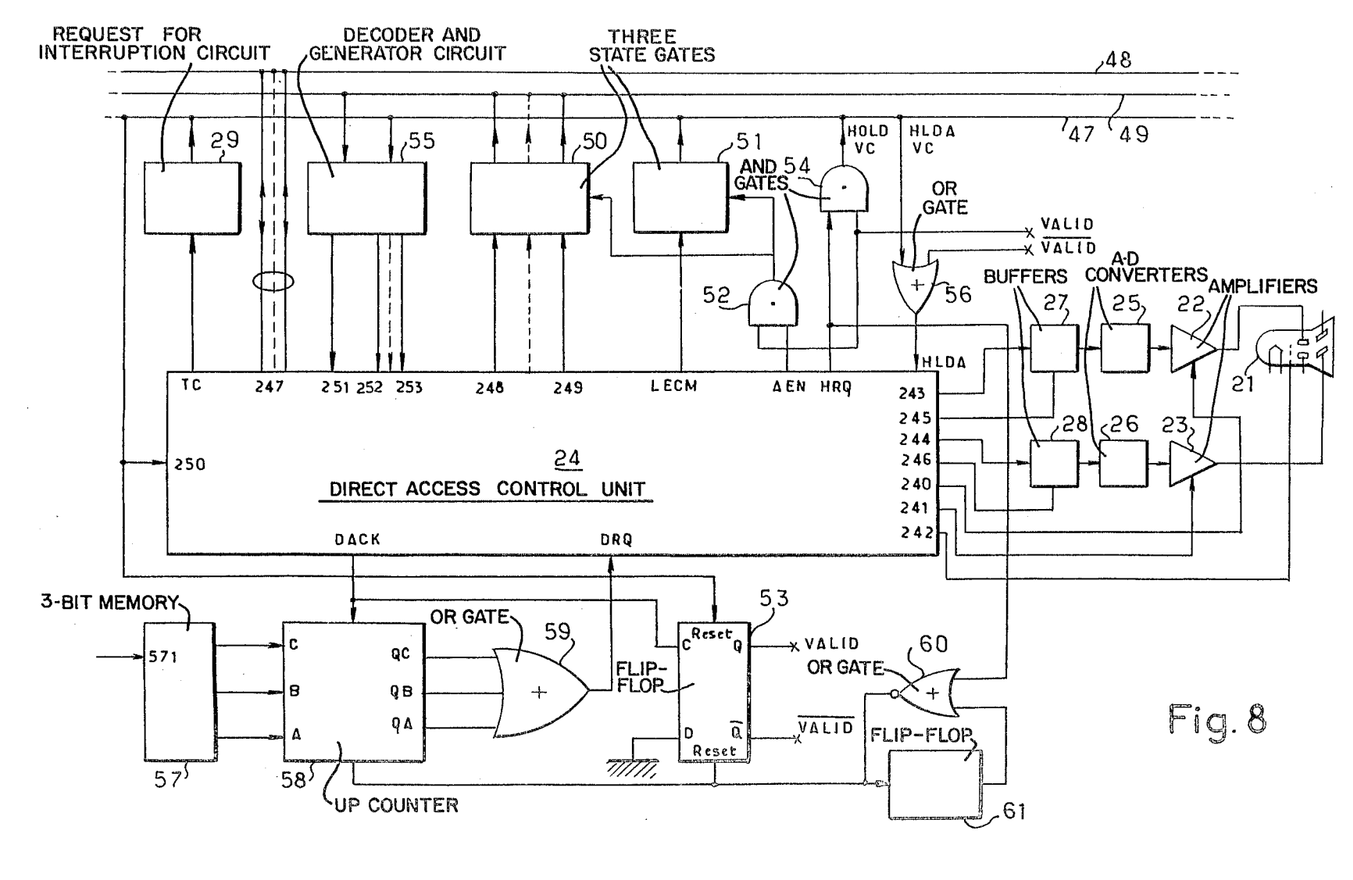

A description will now be given, with reference to FIG. 8, of a display device comprising a cathode-ray tube 21 whose Y-plates are activated by a programmable gain amplifier 22 and whose X-plates are activated by a programmable gain amplifier 23. The gain programme is supplied by outputs 240-241 of a direct access to memory controller 24 whose output 242 is connected to the control electrode of the cathode-ray tube. The inputs of amplifiers 22 and 23 are connected respectively to 10-bit digital-to-analog converters 25-26 supplied by buffer register 27-28. These have inputs connected to the respective data outputs 243 and 244 of the controller 24 and to control outputs 245 and 246.

Controller 24, of known, type, comprises data inputs or circuits 247, a TC output connected to a logical request for interruption circuit 29, 16 memory address outputs 248-249 and outputs (LECM, AEN, HRQ and DACK). It moreover comprises a return to zero input 250 connected to one of the lines 47 of the service signals of the bus of the central unit of the micro-processor. This bus comprises data lines 48 and address lines 49. Outputs 247 are directly connected to lines 48, while lines 248-249 are connected to lines 49 via a set of gates with three states (0, 1 and disconnected) 50. Similarly, output LECM is connected to one of lines 47 via a three-state gate 51. Output AEN is connected to one of the inputs of an AND gate 52, whose output controls gates 50 and 51 and whose other input is connected to the VALID output of a flip-flop 53. Output HRQ is connected to an input of an AND gate 54 whose output is connected to one of lines 47 and whose other input is connected to the VALID output mentioned above.

Inputs 251, 252, 253 of controller 24 are connected to a peripheral address decoder and microcommand generator circuit 55, whose inputs are connected to lines 49 and 47. An input HLDA of controller 24 is connected to the output of an OR gate 56, one input of which is connected to the $\overline{\text{VALID}}$ output of flip-flop 53 and the other input of which is connected to one of lines 47.

A 3-bit memory 57 (of the locking circuit type) receives on its input 571 a signal which defines a reduction factor, as will be explained later. Its three outputs are respectively connected to the three CBA inputs of a deducting counter 58, whose three outputs QC, QB, QA are connected to the three inputs of an OR gate 59. The output of gate 59 is connected to a DRQ input of controller 24. The DACK output is connected, on the one hand to a deduction control input of counter 58 and on the other hand to a control input C of flip-flop 53. The latter's return to zero input is connected to one of lines 47, and its initial state determination input is connected to the output of a reversing OR gate 60, which output is also connected to the load input of counter 58 and to the input of a monostable flip-flop 61. The output of flip-flop 61 is connected to one of the inputs of gate 60, whose other input is connected to the HRQ output of controller 24.

The memory space available in the micro-processor is divided into three zones of 4 kilo-octets each, each allotted to one of the three scalar curves to be displayed. The length of zone mentioned above represents about 8 seconds of recording for a sampling frequency of 500 Hz.

The three curves X, Y and Z will be displayed successively.

Taking one of these three zones, the samples coded by the analog-to-digital converter (8, FIG. 1) are stored sequentially in the memory zone in question, from start pointer DEBDON. Initially DEBDON=DZON (start of zone). Every time a disturbance of the signal is detected, or the operator presses the "triggering" key, the DEBDON pointer is re-initialised by making it point to the last sample stored (DEBDON←PC(tp)), PC being the current pointer and tp the time of disturbance. When the whole of the memory zone allotted has been filled, and if the DEBDON pointer is different from DZON, data continue to be stored starting from DZON until the current pointer PC reaches DEBDON (which means that a sequence of 8 seconds has just been recorded without detecting any disturbance or any intervention by the operator). Samples of each curve are therefore stored in a circular queue structure.

If the portion of the curve comprised between D VISU and F VISU (FIG. 9) is to be displayed on the screen of the oscilloscope, in the standard way: the curve is stored between DEBDON and PC. Generally (F VISU - D VISU), i.e. the number of addresses to be scanned (NAB) is a power of 2 (e.g. $2^{10}$ in the case considered where the output converters 25, 26, FIG. 8 are 10-bit converters).

The horizontal register (28, FIG. 8) is initialised at 0 (left of the screen) and the information contained at the address D VISU is transferred to the vertical register (27). All the other points contained between D VISU and F VISU are then transferred to the vertical register, the horizontal register being incremented by one unit at each transfer. When F VISU is reached, the image has been displayed once. It has to be touched up, i.e. the foregoing operation has to be repeated as often as possible, at least 30 times a second, in order not to get the impression that the image is flickering.

Transfers are made in "direct access to the memory mode" (the only process which can be used in practice to display 30 times a second the image of 3 curves of 1024 points each, i.e. about 100,000 points per second).

A problem arises when the zone to be displayed straddles FZON, DZON. In this case, the image of each curve has to be regarded as 2 sub-images, one being the sub-image of the curve stored between D VISU and FINZON and the other being the sub-image of the curve stored between DEBZON and F VISU.

The way in which a display with image traverse effect is carried out will now be described. After having displayed the zone comprised between DVISU and FVISU, before each touch-up of the image, the DVISU pointer is moved by a quantity Δ and the zone comprised between the DVISU' and FVISU' addresses so defined is displayed. The image appears to have slipped towards the left of the screen by a quantity Δ. The speed of slip is therefore a function of the choice of this quantity Δ.

When the signal is to be displayed in real time, the very last seconds of the current recording must be shown on the screen. In practice, FVISU must coincide roughly with the current pointer PC pointing to the memory location where the last recorded sample has been stored. Since the length of display of a curve (on average 10 ms) is greater than the sampling time (in principle 2 ms), while the zone comprised between DVISU and FVISU is being display, several samples will be stored. If, for each further display, DVISU is moved by the quantity corresponding to that number of samples, perfect synchronisation is, on average, ensured between the speed of apparent traverse of the curve on the screen and the true speed, such as it might be obtained with a multi-track recorder. It is, of course, the central unit which calculates the appropriate number.

The lag assumed by the displayed curve in relation to the recorded curve (on average 4 to 6 points) comes from the fact that the two data acquisition and curve image output processes are completely dissociated, which is essential with a device with direct memory access.

When the image traverse has to be able to be controlled by the operator, the latter must be able to modify $\Delta$ to obtain either traverse to the left ($\Delta > 0$) or traverse to the right ($\Delta < 0$). By adjusting the absolute value of $\Delta$, he can make the image traverse more or less quickly. The value of $\Delta$, which can be applied by the operator by different means, is transmitted to the micro-processor which takes it into account in determining the successive addresses DVISU' - FVISU'.

To obtain an effect of reduction of the size of the curves in a horizontal direction, only one point out of 2 or one point out of 4, etc., of the contents of the memory zone is transferred to the vertical register, the horizontal register being incremented as if no reduction were wanted (i.e. in the manner set out above and corresponding or not corresponding to an image traverse).

To obtain a magnifying-glass effect, the definition of the horizontal converter (25, FIG. 8) is artificially reduced. The apparent step of this converter will be the base step multiplied by the magnifying-glass factor, e.g. 2 or 4, etc. For this purpose, a programmable gain amplifier (23, FIG. 8) is used at the output, which is controlled by controller 24.

An image of the horizontal register can also be stored, which is incremented at each magnifying-glass factor transfer (by 2 or 4, for example).

It is often quicker, for small magnifying-glass factors, to generate intermediate horizontal lines (where microcommands for incrementing the horizontal register are available). In this latter case, 1024 points are still displayed, but only 512 or 256 addresses are scanned.

In the case of a curve reduction, the number of words to be transferred to the vertical register will always be equal to the maximum number of steps of the output converter, i.e. 1024 in the example under consideration.

In the case of a "magnifying-glass" effect, the number of words to be transferred is equal to the quotient of said number by the magnifying-glass factor.

The working of the device in FIG. 8 will now be described briefly, in order to explain what elements have had to be added to a standard display controller to allow for the reduction function.

When a voltage is applied to the device, a return to zero signal is transmitted to controller 24 and flip-flop 53. The required reduction factor, which has been transmitted at 571 by the central unit or from a control element available to the operator, is loaded into counter 58. In fact, the load input of the latter is enabled by the output of gate 60, which is at 1 level because HRQ is at 0 level. The HRQ signal, which corresponds to the despatch of a request for interruption with hold state sent by controller 24 to the central unit, is in fact not yet enabled. The counter being loaded, at least one of its outputs enables DRQ, i.e. a request to controller 24 to look for a datum in the memory. The start address of the zone to be displayed and the word count are then sent to the controller (at 247) which also receives (at 252-253) the order to launch the operation. Controller 24 then enables HRQ which is transmitted to the central unit (the VALID output being at 1 level since the end of the return to zero, gate 54 transmits a 1 level at its output). The central unit responds to the request for interruption with the signal HLDA which is transmitted to controller 24 by OR gate 56. The controller then commands the reading of the stored addresses, by means of the LECM signals, which are only transmitted to one of lines 47 if gate 51 is enabled by the output from gate 52. Now the latter is itself enabled by the VALID signal and the AEN signal, which is an address enabling signal which goes to 1 every time controller 24 is ready to specify the memory address where the reading will be made. Gates 50, which transmit the addresses where the reading is to be made, are enabled at the same time. Once the transfer of the contents of the memory word addressed is complete, the DACK signal rises and its first positive front tips flip-flop 53, so that the $\overline{\text{VALID}}$ output goes to 1 level. The result is that gate 54 ceases to be enabled (therefore the HRQ signal is not longer transmitted to the central unit). The HLDA signal will then cease to be supplied by the central unit, but OR gate 56 nevertheless continues to enable the HLDA input of controller 24, so that the latter will continue to operate. The rising of the DACK signal has controlled a deduction of one unit by counter 58, but DRQ is still enabled (assuming, as a guide, that the reduction factor is equal to 4). The controller will thus increment the horizontal register by one unit. AEN remains enabled, but since the VALID input of gate 52 is at 0 level, gates 50-51 are locked and no reading is made in the memory. The DACk signal falls back after each increment and, in the case under consideration, this process occurs four times, following which the deduction counter 58 is at zero, so that DRQ falls back. Controller 24 then ceases operating.

When the HRQ signal was emitted, monostable 61 was set for a pre-determined time, e.g. 10 microseconds. So long as it remains set, the load control input of counter 58 is inhibited, even when HRQ has fallen back (gate 60). A further loading is therefore impossible until a time of 10 microseconds has elapsed. In the case of a high reduction factor, the HRQ signal falls back after a time exceeding 10 microseconds and it is only then that the load control input of counter 58 is enabled. Because of monostable 61, in all cases there is therefore a time of at least 10 microseconds between two requests for direct access to the memory; during this time, the central unit is, moreover, only interrupted until the VALID signal falls back, i.e. for a relatively short time.

The display procedure and device just described make it possible, during data acquisition, to follow this acquisition in real time, watching the curves move across the screen from right to left, the image of the last 4 seconds of the recording being constantly obtained. This operation is carried out on compressed signals in non-linear fashion, so that sensitivity is increased in the middle of the screen. Monitoring of the appearance of disturbances or a myogram is thereby facilitated.

During verification operations, on the other hand, the signal is not compressed, which leaves the scale of the relative values intact; but because of normalisation, the curves occupy the whole of the portion of the screen which is allotted to them. The operator also has available a reduction or magnifying-glass effect, allowing him to examine in detail certain irregularities in the graph and he can make the image move to the left or the right at greater or lesser speed, or freeze it.

It goes without saying that various modifications of details may be made to the apparatus described and shown, without departing from the spirit of the invention.

We claim:

1. A portable apparatus for the acquisition and pre-processing of vectocardiographic data, said apparatus comprising: a plurality of electrodes arranged according to Frank's orthogonal system; first means having a plurality of inputs connected to the respective electrodes for multiplexing and pre-amplifying the said vectocardiographic data; second means, including a Frank resistive network connected to the said first means, for converting the said data into scalar signal components having a base line; third means, connected to the said second means, for amplifying the said scalar signal components; analog-to-digital converter means, connected to the said third means, for converting the amplified scalar si signal components into digital signals; calibration means, including an analog calculation network, for generating calibration signals of predetermined amplitude and for applying the said calibration signals to the said inputs of the first means under the control of control signals during a predetermined time interval; micro-processor means for processing the said digital signals, for providing the said control signals to the input of said calibration means, for analysing the response of the first, second and third means to said calibration signals, and for deriving from the said response a determination of the gain and pass-band of the said first, second and third means, said microprocessor means further applying clamping signals to said third means for clamping the said base line to zero at the beginning and end of the said predetermined time interval and, subsequently, at fixed time intervals each corresponding to a data acquisition sequence.

2. An apparatus according to claim 1, wherein the said third means comprise fixed gain amplifiers, the said apparatus further comprising means, connected to the said analog-to-digital converter means, for effecting digit compression of said vectocardiographic data.

3. An apparatus according to claim 2, wherein the said third means further comprise differential amplifiers each having a negative input and a positive input, the said positive input being connected to the respective fixed gain amplifier and sample-and-hold circuits each having an input and an output, the said output of the sample-and-hold circuit being connected to the negative input of the respective fixed gain amplifier and means connecting each fixed gain amplifier to the input of the respective sample-and-hold circuit.

4. An apparatus according to claim 2, wherein the analog-to-digital converter means have eleven outputs, on which the eleven bits of increasing significance of the said digital signals are respectively provided and a twelfth output on which the signal bit of the said digital signals is provided and the said digit compression means includes a priority coder having inputs of increasing priority order respectively connected to the fifth to eleventh outputs of the analog-to-digital converter means, the said priority coder having three outputs and a parallel shift network having four inputs respectively connected to the first to fourth outputs of the analog-to-digital converter means and six further inputs respectively connected to the fifth to tenth outputs of the analog-to-digital converter means, said parallel shift network having six outputs, the six outputs of the parallel shifting network, the three outputs of the priority coder and the twelfth output of the analog-to-digital compressor means together forming ten outputs of the said digit compression means.

5. An apparatus according to claim 1, said apparatus further comprising detecting means for applying a clamping signal to said third means each time the capacity of the analog-to-digital converter is exceeded.

6. An apparatus according to claim 1, said apparatus further comprising means for determining the peaks of the QRS complexes of the said scalar signal components, said means including: three high-pass filters connected to the said third means; three amplifiers connected to the respective filters and arranged to transmit the respective absolute values of the said scalar signal components; an adding amplifier connected to the said three amplifiers and a peak detector connected to the said adding amplifier, said peak detector comprising a capacitor which charges, at each peak, to the peak value of the output voltage of the adding amplifier and discharges through an impedance adjusted so that, between two successive peaks, the new charge shall have reached a pre-determined fraction of the one correspondingto the peak value and means for generating a pulse every time the output voltage of the adding amplifier becomes higher than the voltage at the terminals of the capacitor.

7. An apparatus according to claim 1, wherein said micro-processor means has a data memory in which the data corresponding to the said digital signals are stored, the said memory being divided into zones of the same length each allotted to one of the said scalar signal components and managed in circular queue form, from a start pointer, the apparatus further comprising cathode-ray tube means for displaying the said data under the form of curve images, first register means controlling the vertical deflexion in the said tube, second register means for controlling the horizontal deflexion in said tube; means for sequentiallytransferring the contents of each zone into the first register means, means for incrementing by at least one unit the second register means at each transfer operation, the complete transfer of any predetermined portion of curve being repeated at least thirty time per second.

8. An apparatus according to claim 7, wherein means are further provided for effecting before each of said successive complete transfer operations, an adjustable systematicshift of the said start pointer, in order to make the image displayed move in one direction or the other.

9. An apparatus according to claim 7, wherein the micro-processor includes means for controlling said shift so that it will correspond to the portion of curve formed during the time of a complete transfer operation and thus to synchronise the movement of the image displayed with the real movement of the curve.

10. An apparatus according to claim 7, wherein the said sequential transfer means are adapted to transfer only one address out of n from the zone into the first register, n being a wholereduction factor.

11. An apparatus according to claim 10, wherein the said sequential transfer means include a direct memory access controller and means, cooperating with the said controller, for storing the reduction factor and enabling the working of the controller for a number of data-finding operationsin the memory corresponding to said factor and means of disabling the connection between the controller and the memory during said operations, to the exclusion of the first.

12. An apparatus according to claim 11, wherein said means for storing the reduction factor include means of preventing the storage of a new reduction factorebefore a pre-determined time has elapsed, counted from the time when a reduction factor is stored.

13. An apparatus according to claim 7, wherein the said means for incrementing the second register provide an apparent incrementation of the said second register in steps of at least two units.

* * * * *